United States Patent [19]

Comins et al.

[11] Patent Number: 5,321,140
[45] Date of Patent: Jun. 14, 1994

[54] PYRIDINECARBOXALDEHYDE D-RING INTERMEDIATES USEFUL FOR THE SYNTHESIS OF CAMPTOTHECIN AND CAMPTOTHECIN ANALOGS

[75] Inventors: Daniel L. Comins; Matthew F. Baevsky, both of Cary, N.C.

[73] Assignee: North Carolina State University, Raleigh, N.C.

[21] Appl. No.: 17,648

[22] Filed: Feb. 12, 1993

Related U.S. Application Data

[62] Division of Ser. No. 927,220, Aug. 10, 1992, Pat. No. 5,200,524, which is a division of Ser. No. 632,970, Dec. 20, 1990, Pat. No. 5,162,532.

[51] Int. Cl.$^5$ .............................. C07D 213/64
[52] U.S. Cl. .................................. 546/298
[58] Field of Search .......................... 546/298

[56] References Cited

U.S. PATENT DOCUMENTS 4,578,381  3/1986  Uchida et al. ............... 514/233
4,894,456  1/1990  Wall et al. .................. 546/41

FOREIGN PATENT DOCUMENTS 0325247  7/1989  European Pat. Off. .

OTHER PUBLICATIONS

R. E. Lyle et al., *Abstracts*, 23d International Congress of Pure and Applied Chemistry (Boston, Mass. 1971), p. 67.

J. Plattner et al., "Synthesis of Some DE and CDE Ring Analogs of Camptothecin," *J. Amer. Chem. Soc.*, 94, No. 24, 8613–8615 (1972).

M. Doyle et al., *J. Am. Chem. Soc.* 94, No. 10, 3659 (1972).

R. Lyle et al., *J. Org. Chem.* 37, No. 24, 3967 (1972).

R. Lyle et al., *J. Org. Chem.*, 38, No. 19, 3268 (1973).

D. Portlock et al., "Studies of the Photocyclization of Some 1-(Haloarylmethyl)pyridinium Salts," *J. Org. Chem.* 38, No. 13, 2351–2355 (1973).

(List continued on next page.)

*Primary Examiner*—Bernard Dentz
*Attorney, Agent, or Firm*—Bell, Seltzer, Park & Gibson

[57] ABSTRACT

Compounds of Formula I

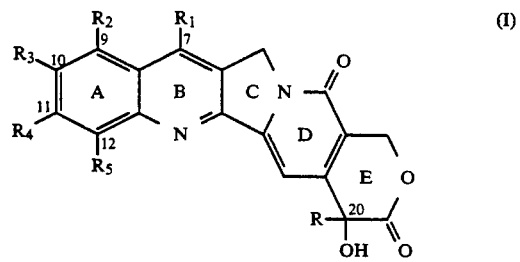

are made in accordance with the following scheme:

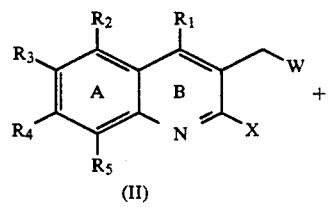

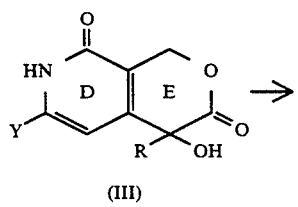

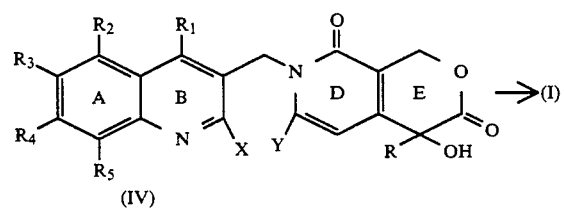

wherein R may be loweralkyl; $R_1$ may be H, loweralkyl, loweralkoxy, or halo; $R_2$, $R_3$, $R_4$, and $R_5$ may each independently be H, amino, hydroxy, loweralkyl, loweralkoxy, loweralkylthio, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom; Y is H and W and X are halogen. Also disclosed are novel processes for making starting materials for the scheme given above, and novel intermediates employed in these processes.

9 Claims, No Drawings

OTHER PUBLICATIONS

T. Sugasawa et al. "Experiments on the Synthesis of di-Camptothecin. Synthesis of a D-E Ring Analog of Camptothecin and a Total Synthesis of Recinine," *Chem. Pharm. Bull.* 22, No. 4, 763-770 (1974).

"Heterocyclic Compounds: Pyridine and Its Derivatives", vol. 14, Supplement Part 3 (John Wiley & Sons, Inc., Ed. Abramovitch), pp. 745-753 (1974).

J. Bristol et al., *Journal of Medicinal Chemistry* 18, No. 5, 535 (1975).

D. Comins, Ph.D. Thesis, University of New Hampshire, Durham, N.H., pp. 25-29 (1977).

A. Schmidt, *Aldrichimica Acta* 14, No. 2, 31 (1981).

J. Cai and C. Hutchinson, *The Alkaloids XXI*, 101 (Academic Press 1983).

D. Comins and J. Brown, *J. Org. Chem.*, 49, No. 6, 1078 (1984).

J. March, "Advanced Organic Chemistry: Reactions, Mechanisms, and Structure," Third Edition, (John Wiley & Sons, Inc.) pp. 510-511 (1985).

D. Comins and D. LaMunyon, *Tetrahedron Letters* 29, No. 7, 773 (1988).

D. Comins and J. Brown, *J. Org. Chem.* 54, No. 15, 3730 (1989).

R. Larock, "Comprehensive Organic Transformations: A Guide to Functional Group Preparations," (VCH Publishers, Inc., New York, N.Y.) pp. 467-468 (1989).

R. Larock, "Comprehensive Organic Transformations: A Guide to Functional Group Preparations," (VCH Publishers, Inc., New York, N.Y.) pp. 501-504 (1989).

D. Comins and M. Killpack, *J. Org. Chem.* 55, No. 1, 69 (1990).

R. Grigg et al., *Tetrahedron* 46, No. 11, 4003 (1990).

"Natural Products Chemistry," vol. 2 (Academic Press, Inc., Ed. K. Nakanishi et al.), pp. 358-361 (1973).

"Natural Products Chemistry," vol. 3 (Academic Press, Inc., Ed. K. Nakanishi et al.), pp. 573-574 (1979).

PYRIDINECARBOXALDEHYDE D-RING INTERMEDIATES USEFUL FOR THE SYNTHESIS OF CAMPTOTHECIN AND CAMPTOTHECIN ANALOGS

This application is a divisional of U.S. patent application Ser. No. 07/927,220 filed Aug. 10, 1992 now U.S. Pat. No. 5,200,524, which is a divisional of Ser. No. 07/632,970 as of Dec. 20, 1990 U.S. Pat. No. 5,162,532.

FIELD OF THE INVENTION

The present invention provides a parallel synthesis of camptothecin and camptothecin analogs via novel intermediates at high yields.

BACKGROUND OF THE INVENTION

Camptothecin (Chem. Abstracts Registry No. 7689-03-4) is a naturally occuring compound found in *Camptotheca acuminata* (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of syntheses for camptothecin are known. Several routes are reviewed in *Natural Products Chemistry*, Vol. 2, 358–361 (K. Nakanishi, T. Goto, S. Ito, S. Natori and S. Nozoe eds.) and in J. Cai and C. Hutchinson, Camptothecin, in *The Alkaloids*, Vol. XXI, 101–137 (Academic Press 1983). The biosynthesis of camptothecin is described in *Natural Products Chemistry*, Vol. 3, 573–574 (K. Nakanishi et al. eds.). A recent synthetic route is described in U.S. Pat. No. 4,894,456 to Wall et al. (see also references cited therein).

A problem with prior methods of synthesizing camptothecin is that they are largely linear syntheses. Such syntheses provide low yields of the final product because of the sequential loss in product during each step of the total synthesis. Parallel syntheses (i.e., a strategy in which two synthetic paths are followed separately and the products thereof combined to form the final product) provide higher yields, but few such syntheses have been available for camptothecin. Accordingly, an object of the present invention is to provide a parallel synthetic method for making camptothecin and analogs thereof.

SUMMARY OF THE INVENTION

The present invention provides a method of making compounds of Formula I below:

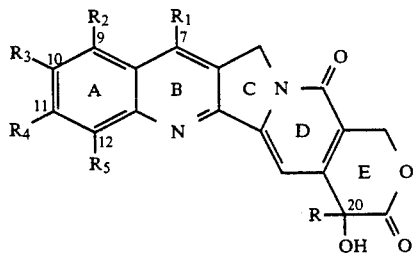

wherein
R may be loweralkyl, preferably ethyl.
$R_1$ may be H, loweralkyl, loweralkoxy, or halo (e.g., chloro). Preferably $R_1$ is H.
$R_2$, $R_3$, $R_4$, and $R_5$ may each independently be H, amino, hydroxy, loweralkyl, loweralkoxy, loweralkylthio, di(loweralkyl)amino, cyano, methylenedioxy, formyl, nitro, halo, trifluoromethyl, aminomethyl, azido, amido, hydrazino, or any of the twenty standard amino acids bonded to the A ring via the amino-nitrogen atom (numbering in Formula I is by the Le Men-Taylor numbering system and rings are lettered in the conventional manner. See J. Cai and C. Hutchinson, supra at 102).

At least two of $R_2$, $R_3$, $R_4$, and $R_5$ may be H, and in a preferred embodiment $R_2$, $R_4$, and $R_5$ are H.

Preferably: $R_2$ is H or amino; $R_3$ is H or hydroxy; $R_4$ is H; and $R_5$ is H.

In the invention, a compound of Formula I is produced according to scheme A below, where Y is H, $R_1$ through $R_5$ are as given in connection with Formula I above, X is halogen, preferably bromo or iodo; and W is halogen, preferably chloro.

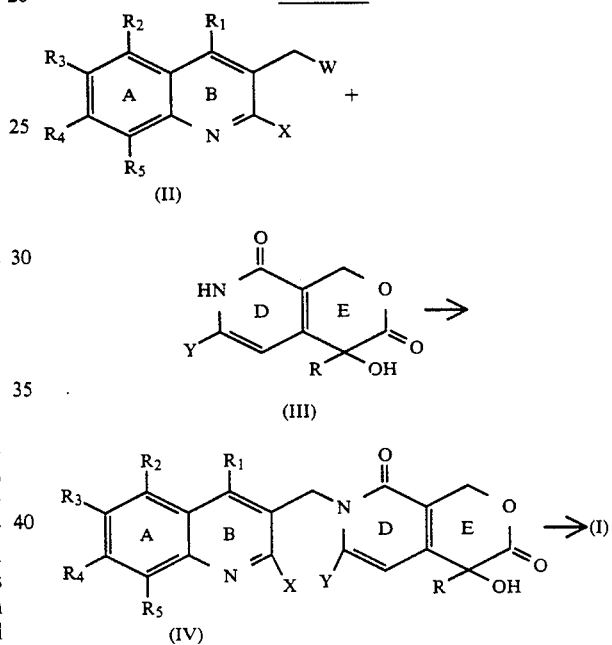

DETAILED DESCRIPTION OF THE INVENTION

As used herein, the term "loweralkyl" means a linear or branched alkyl group with 1–8, preferably 1–4, carbon atoms, such as methyl, ethyl, propyl, isopropyl, n-butyl, tert-butyl, hexyl, and octyl. This definition also applies to a loweralkyl moiety in the loweralkoxy, loweralkylthio, and di(loweralkyl)amino groups. Thus, examples of loweralkoxy groups are methoxy, ethoxy, propoxy, sec-butoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

Substituents on the "A" ring of the compounds disclosed herein may be joined together to form a bifunctional substituent such as the methylenedioxy group.

Methylenedioxy substituents may be bonded to any two consecutive positions in the A ring, for example, the 9,10, the 10,11, or the 11,12 positions.

Substituents which are standard amino acids may be any of the twenty amino acids commonly found in naturally occuring proteins, and are well known in the art. These provide a substituent of the formula —NHCHRCOOH, with R being the side chain of any of the twenty standard amino acids. The amino acids may be of any configuration, but preferably have an (L) configuration.

A compound of Formula I is produced in accordance with Scheme A below by alkyating a pyridone of Formula III with a chloromethylquinoline of Formula II to produce a compound of Formula IV, and then cyclizing the compound of Formula IV to yield the compound of Formula I.

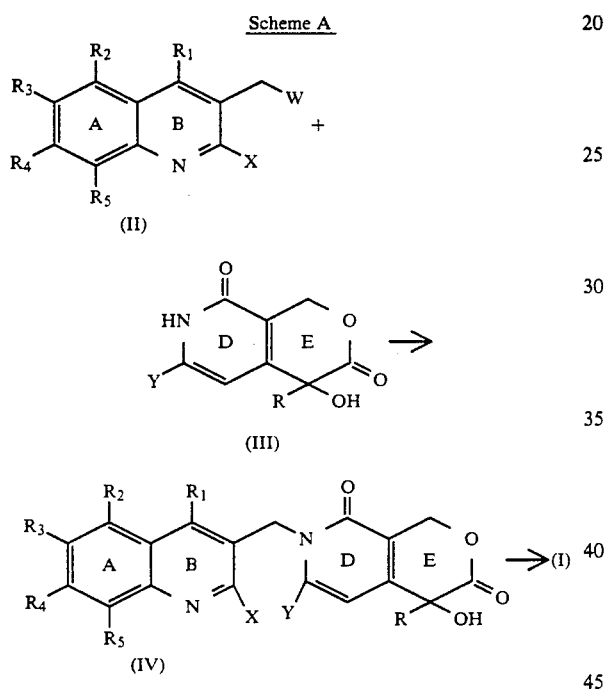

In Scheme A: Y is H; R and $R_1$ through $R_5$ are as given in connection with Formula I above; X is halogen, preferably bromo or iodo; and W is halogen, preferably chloro.

The starting materials of Scheme A, the compounds of Formula II and III, are prepared in accordance with Schemes B and C below.

The pyridone of Formula III may be alkylated with a halomethylquinoline of Formula II in a suitable solvent, such as a polar protic solvent (e.g., isopropyl alcohol, ethanol, methanol), an aprotic solvent (e.g., 1,2-dimethoxyethan, tetrahydrofuran, toluene, acetonitrile, or dimethylformamide) or alternatively in an aqueous solution in the presence of a phase transfer catalyst. The reaction is preferably carried out under mildly basic conditions, to minimize attack on the pyridone ring oxygen. The reaction may be carried out as a single step, or may conveniently be carried out in two stages by, first, forming the anion of of the pyridone by addition of an alkali earth salt (e.g., potassium tert-butoxide) at about room temperature, and then adding the halomethylquinoline to the reaction solution and heating the solution between about 60° to about 100° Centigrade for 4–24 hours.

The compound of Formula IV may be cyclized to yield the compound of Formula I by an intramolecular Heck reaction. The reaction is carried out in the presence of a palladium catalyst (e.g., palladium acatate) under basic conditions in a polar aprotic solvent such as acetonitrile or dimethylformamide. A phase transfer catalyst such as a tetraalkylammonium halide salt is preferably included. The reaction should be carried out in an inert atmosphere, such as under argon. The reaction mixture may be heated to a temperature between about 50° to about 100° C. for about 1 to 24 hours. Variations on these conditions will be aparent from the literature on the Heck reaction. See, e.g., R. Grigg et al. *Tetrahedron* 46, 4003–4008 (1990).

The compounds of Formula II may be prepared in accordance with Scheme B below, where $R_1$ through $R_5$ are as given in connection with Formula I above, and X is Bromo or Iodo, preferably Iodo.

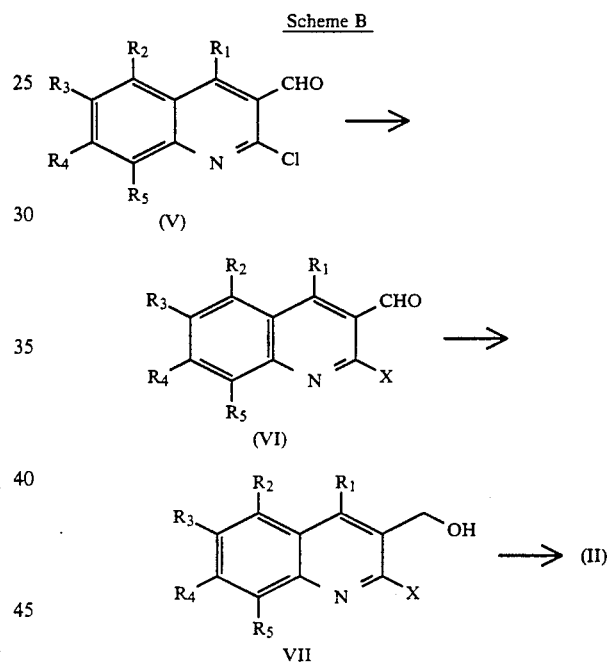

The starting materials in Scheme B, the compounds of Formula V, are made by known techniques, such as by chlorination of a quinoline. See, e.g., *Progress in Heterocyclic Chemistry* 2,180 (H. Suschitzky and E. Scriven eds. 1990). In the alternative, compounds of Formula V may be made from the substituted acetanilide as described by O. Meth-Cohn et al., J. Chem. Soc. Perkin Trans. I 1981, 1520.

The halo group on the carboxaldehyde of Formula V is exchanged with an Iodo or Bromo (preferably Iodo) to produce the carboxaldehyde of Formula VI. The exchange reaction may be carried out in acetonitrile in the presence of a catalytic amount of a strong acid, such as HCl, by heating the reaction mixture to between about 70° to about 90° C. for at least about 4 hours.

The carboxaldehyde of Formula VI is then reduced to produce the hydroxymethylquinoline of Formula VII. The reaction is carried out with a mild reducing agent to avoid reducing the quinoline ring, at a temperature of from about 0° to about 25° C., in an alcohol solvent. An alternative route for producing a compound of Formula VII is disclosed in N. Narasimham et al., *J. Chem. Soc., Chem. Commun.*, 1985, 1368–1369.

A compound of Formula II is produced from the hydroxymethylquinoline of Formula VII in accordance with conventional procedures in a solvent in which the reactants are soluble, such as dimethylformamide. The reaction is preferably carried out at lower temperatures to provide a higher yield.

The compounds of Formula III above are preferably prepared in accordance with Scheme C below, wherein R is as given in connection with Formula I above, $R_6$ and $R_7$ are loweralkyl, preferably methyl, $R_8$ is loweralkyl, preferably ethyl, Y is Cl or H, and Z is halo, preferably bromo or iodo.

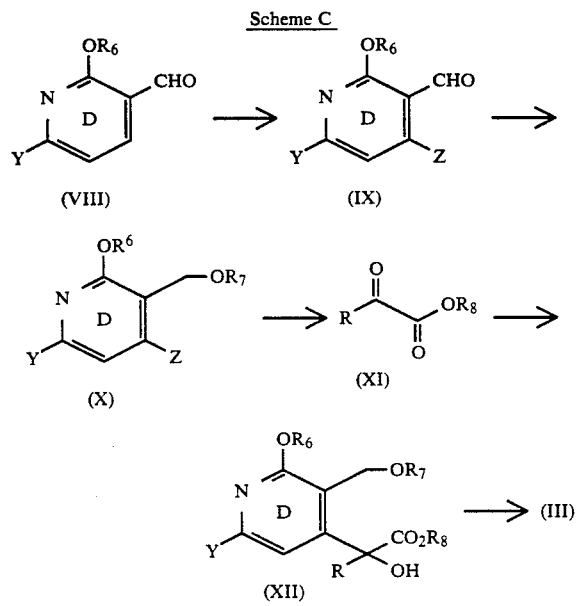

Scheme C

The starting materials for Scheme C, the compounds of Formula VIII, may be prepared in accordance with known techniques. For example, the synthesis of 2-methoxy-3-pyridinecarboxaldehyde is disclosed in D. Comins and M. Killpack, *J. Org. Chem.* 55, 69–73 (1990).

In Scheme C, the carboxaldehyde of Formula VIII is halogenated to produce the 4-halo-3-pyridinecarboxaldehyde of Formula IX. Halogenation at the 4-position may be carried out by reacting the carboxaldehyde of Formula VIII with a lithiated diamine, such as lithiated N,N,N'-trimethylethylenediamine, in dimethoxyethane or tetrahydrofuran to protect the aldehyde and direct subsequent C-4 lithiation, and by then lithiating the C-4 position of the pyridine with a suitable lithiating reagent, such as n-butyllithium. See D. Comins and M. Killpack, supra. The C-4 lithiated pyridine intermediate is preferably halogenated by adding the intermediate to a solution of iodine or bromine in a polar or nonpolar organic solvent, preferably at a temperature of at least as low as about −70° C.

The compound of Formula IX is reduced in an alcoholic acidic media in the presence of a trialkylsilane to yield the alkoxymethylpyridine of Formula X. The acid should be a strong acid, such as sulfuric or trifluoroacetic acid. At least about 2 molar equivalents of a suitable alcohol (e.g., methanol, ethanol, tert-butanol) should be included to convert the aldehyde to the ether. Reference may be made to the literature on the silane reduction of aldehydes for conditions and variations on this reaction. See, e.g., M. Doyle et al., *J. Am. Chem. Soc.* 94:10, 3659–3661 (1972).

The compound of Formula X is lithiated at the C-4 position with a lithiating agent such as n-butyllithium, and then reacted with a compound of Formula XI such as an alkyl α-ketobutyrate (e.g., methyl α-ketobutyrate, ethyl α-ketobutyrate, tert-butyl α-ketobutyrate) to produce the compound of Formula XII in essentially the manner described by R. Lyle et al., *J. Org. Chem.* 38, 3268–3271 (1973). The reaction may be carried out in a tetrahydrofuran or ether solvent at a temperature of at least as low as about −50° C., with the alkyl α-ketobutyrate being added to the reaction solution as a single aliquot.

The compound of Formula XII is then cyclized to yield the compound of Formula III. Cyclization may be carried out by reacting the compound of Formula XII with bromo- or iodotrimethylsilane (preferably iodotrimethylsilane) in a neutral or polar aprotic solvent such as acetonitrile, followed by reaction with a strong acid solution to cleave the ethers and yield the compound of Formula III (the ring forming spontaneously upon cleavage of the ethers). The bromo- or iodotrimethylsilane is preferably generated in situ in accordance with known techniques, such as by the reaction of chlorotrimethylsilane with a halogen salt or elemental halogen. See A. Schmidt, *Aldrichimica Acta* 14, 31–38 (1981).

When Y is halo in the compound of Formula III, the compound may be hydrogenated by any suitable technique, preferably by catalytic hydrogenation in the presence of a palladium catalyst in a hydrogen atmosphere under pressure (e.g., at least three atmospheres). See generally J. March, *Advanced Organic Chemistry*, 510–511 (3d. Ed. 1985).

As alternatives to Scheme C, a compound of Formula III, where Y is H, may be prepared in the manner described in D. Comins, Ph.D. Thesis, University of New Hampshire, Durham, N.H., at 25–29 (1977), and as described in Lyle et al., *J. Org. Chem.* 38, 3268–3271 (1973).

The discussion herein is, for simplicity, given without reference to sterioisomerism. However, the compounds of Formula I have an asymmetric carbon atom at the C-20 position. Thus, the present invention is concerned with the synthesis of both (i) racemic mixtures of the compound of Formula I and (ii) enantiomeric forms of the compound of Formula I, particularly the 20-(S) form. The resolution of racemates into enantiomeric forms can be done in connection with the last step of the process, or in preceeding steps involving the synthesis of an intermediate having an asymmetric carbon atom, by known procedures. For example, the racemate may be converted with an optically active reagent into a diasteriomeric pair, and the diasteriomeric pair subsequently separated into the enantiomeric forms.

Specific examples of compounds which may be prepared by the method of the present invention include 9-methoxy-camptothecin, 9-hydroxy-camptothecin, 9-nitro-camptothecin, 9-amino-camptothecin, 10-hydroxycamptothecin, 10-nitro-camptothecin, 10-aminocamptothecin, 10-chloro-camptothecin, 10-methylcamptothecin, 11-methoxy-camptothecin, 11-hydroxycamptothecin, 11-nitro-camptothecin, 11-aminocamptothecin, 11-formyl-camptothecin, 11-cyanocamptothecin, 12-methoxy-camptothecin, 12- hydroxycamptothecin, 12-nitro-camptothecin, 10,11-dihydroxycamptothecin, 10,11-dimethoxy-camptothecin, 7-methyl10-fluoro-camptothecin, 7-methyl-10-chlorocamptothecin, 7-methyl-9,12-dimethoxy-camptothecin, 9,10,11-trimethoxy-camptothecin, 10,11-methylenedioxycamptothecin and 9,10,11,12-tetramethyl-camptothecin.

Compounds of Formula I have antitumor and antileukemic activity. Additionally, compounds of Formula I wherein $R_1$ is halo are useful as intermediates for, among other things, making compounds of Formula I wherein $R_1$ is loweralkyl.

Those skilled in the art will appreciate that additional changes can be made in the compounds of Formula I (see, for examples, J. Cai and C. Hutchinson, supra.), which changes will not adversely affect the new processes disclosed herein and do not depart from the concept of the present invention.

In the Examples which follow, "mg" means milligrams, "M" means Molar, mL means milliliter(s), "mmol" means millimole(s), "BU" means butyl, "THF" means tetrahydrofuran, "h" means hours, "min" means minutes, "C" means Centigrade, "p.s.i." means pounds per square inch, "DMF" means dimethylformamide, "TLC" means thin layer chromatography, and "PLC" means preparative thin layer chromatography.

EXAMPLE 1

6-Chloro- 2-methoxy- 3-pyridinecarboxaldehyde

To a solution of tert-butyllithium (1.7M in pentane, 48.5 mL, 83.0 mmol) in 150 mL of THF at −78° C. was added 6-chloro-2-methoxypyridine ( 8.94 mL, 75.0 mmol) over 5 min. The reaction mixture was stirred at −78° C. for 1 h, then dimethylformamide (7.55 mL, 97 mmol) was added and the mixture was stirred at this temperature for 1.5 h. After the addition of glacial acetic acid (8.6 mL, 150 mmol), the reaction mixture was allowed to warm to room temperature over a 30-rain period, then diluted with ether (200 mL). The organic phase was washed with saturated aqueous NaHCO3 (100 mL) and brine (100 mL), and was dried over MgSO4. Concentration afforded the crude product as a light yellow solid which was recrystallized from hexanes to give 9.6 g (75%) of 6-chloro-2-methoxy-3-pyridinecarboxaldehyde as a white solid: mp 80°–81° C. (top 62°–64 ° C.) (See Dainter, R. S.; Suschitzky, H.; Wakefield, B. J. Tetrahedron Lett. 1984, 25, 5693.). $^1$H NMR (300 MHz, CDCl3) δ 10.31 (s, 1H), 8.07 (d, 1H, J=9 Hz), 7.03 (d, 1H, J=9 Hz), 4.09 (s, 3H); IR (nujol) 1685, 1580, 1565, 1270, 1140, 1090, 1005, 905, 820, 755 cm$^{-1}$.

EXAMPLE 2

6-Chloro-4-iodo-2-methoxy-3-pyridinecarboxaldehyde

To a solution of N,N,N'-trimethylethylenediamine (2.46 mL, 19.23 mmol) in 15 mL of 1,2-dimethoxyethane at −23° C. was added n-BuLi (9.22 mL, 19.23 mmol), and the solution was stirred at −23° C. for 20 min. The mixture was transferred using a double-tipped needle to a solution of 6-chloro-2-methoxy-3-pyridinecarboxaldehyde (3.0 g, 17.5 retool) in 40 mL of 1,2-dimethoxyethane at −23° C. After stirring for 15 rain, n-BuLi (12.6 mL, 26.2 mmol) was added and the dark mixture was stirred an additional 2 h at −23° C. The solution was transferred using a double-tipped needle to a solution of iodine (8.04 g, 31.7 retool) in 40 mL of 1,2-dimethoxyethane at −78° C. After stirring at −78° C. for 30 min, the cooling bath was removed and the reaction mixture was allowed to warm for 20 min, then quenched with water. The mixture was extracted with ether (2×30 mL) and the combined organic layers were washed successively with 30-mL portions of 10% aqueous Na2S2O3, water and brine, and dried over MgSO4. Concentration afforded 4.62 g (89%) of crude product to which was added 50 mL of hexanes. The mixture was stirred and allowed to stand at 5° C. overnight. Filtration gave 2.67 g of 6-Chloro-4-iodo-2-methoxy-3-pyridinecarboxaldehyde as a yellow solid: mp 120°–124° C. Concentration of the hexane washings and purification of the residue by radial preparative thin-layer chromatography ( silica gel, 5% ethyl acetate/hexanes) gave an additional 1.41 g of product (mp 120°–124° C.), raising the total yield of the compound to 78%. Recrystallization from hexanes gave an analytical sample as a bright yellow solid: mp 129°–130° C. $^1$H NMR (300 MHz, CDCl3) δ 10.16 (s, 1H), 7.59 (s, 1H), 4.07 (s, 1H); IR (nujol) 1690, 1350, 1260, 1095, 1010, 900, 840 cm$^{-1}$.

EXAMPLE 3

2-Chloro-4-iodo-6-methoxy-5-(methoxymethyl)pyridine

To a mixture of 6-chloro-4-iodo-2-methoxy-3-pyridinecarboxaldehyde (1.07 g, 3.60 mmol), triethylsilane (0.86 mL, 5.40 mmol) and methanol (0.43 mL, 10.6 mmol) at 0° C. was added trifluoroacetic acid (2.2 mL, 28.6 mmol), and the resulting solution was stirred at 25° C. for 14 h. After dilution with ether (30 mL), saturated NaHCO3 was added until the aqueous phase was rendered basic. The aqueous layer was extracted with ether (10 mL), and the combined ether layers were washed with water (10 mL) and brine (10 mL), and dried (Na2SO4). Concentration gave the crude product which was purified by radial PLC (silica gel, 5% ethyl acetate/hexanes) to afford 2-chloro-4-iodo-6-methoxy-5-(methoxymethyl)pyridine as a White solid (1.05 g, 93%): mp 69°–72° C. Recrystallization from hexanes provided an analytical sample: mp 74°–75° C. $^1$H NMR (300 MHz, CDCl3) δ 7.40 (S, 1H), 4.53 (s, 2H), 3.96 (s, 3H), 3.42 (s, 3H); IR (nujol) 1550, 1300, 1115, 1090, 1020, 940, 905, 830, 720 cm$^{-1}$.

EXAMPLE 4

Ethyl 2-Hydroxy,2-(6'-chloro-2'-methoxy-3'-methoxymethyl-4'-pyridyl )butyrate

To a solution of 2-chloro-4-iodo-6-methoxy-5-(methoxymethyl)pyridine (2.28 g, 7.30 retool) in 50 mL of THF at −90°C. was added n-BuLi (3.46 mL, 8.03 mmol) over 5 min and the resulting solution was stirred at −90° C. for 30 min. Ethyl α-ketobutyrate (1.25 mL, 9.45 mmol) was added, the reaction mixture was stirred at −90° C. for 30 min, then allowed to warm at ambient for 20 min, and quenched with saturated NH4Cl. After removal of most of the solvent under reduced pressure, the residue was taken up in 40 mL of ether, washed with dilute NaHCO3 (15 mL) and brine (15 mL), and was dried over MgSO4. Evaporation of the solvent in vacuo and purification of the residue by radial PLC (10% acetone/hexanes ) afforded ethyl 2-hydroxy-2- ( 6'-chloro-2'-methoxy-3'-methoxymethyl-4'-pyridyl)butyrate (1.53 g, 66% ) as a light yellow, viscous oil. $^1$H NMR ( 300 MHz, CDCl3) δ 7.07 (s, 1H), 4.75 (d, 1H, J=12 Hz), 4.47 (d, 1H, J=12 Hz), 4.24 (q, 1H, J=6 Hz), 4.17 (q, 1H, J=6 Hz), 3.96 (s, 3H), 3.37 (s, 3H), 2.16 (m, 2H), 1.24 (t, 3H, J=6 Hz); IR (film) 3400, 1735, 1580, 1555, 1305, 1235, 1130, 1090, 1020, 905, 830, 730 cm$^{-1}$.

EXAMPLE 5

9-Chloro-7-oxopyrido[5,4-c]-2-oxo-3-ethyl-3-hydroxy-3,6-dihydropyran

To a stirred mixture of the hydroxy ester prepared in Example 4 above ( 1.53 g, 4.82 mmol ) and sodium iodide (2.89 g, 19.3 retool) in dry CH$_3$CN (35 mL) at 25° C. was added dropwise chlorotrimethylsilane (2.45 mL, 19.3 mmol). The resulting solution was heated at reflux for 4 h, the solvent was removed under reduced pressure, and 100 mL of 6N HCl was added to the residue. After heating at a gentle reflux for 4 h, the mixture was stirred at 25° C. overnight, then extracted with six 30-mL portions of CHCl$_3$ containing 5% CH$_3$OH. The combined organic extracts were washed with 40 mL of half-saturated NaCl containing Na$_2$S$_2$O$_3$, followed by 40 mL of saturated NaCl. After drying over Na$_2$SO$_4$, the solvent was removed under reduced pressure and the residue was purified by radial PLC (silica gel, 5% CH$_3$OH/CHCl$_3$) to give 9-chloro-7-oxopyrido[5,4-c]-2-oxo-3-ethyl-3-hydroxy-3,6-dihydropyran (743 mg, 63%) as an off-white solid: mp 205°-207° C. Recrystallization from CHCl$_3$/CH$_3$OH gave an analytically pure sample as a white solid: mp 207°-208° C. $^1$H NMR (300 MHz, CDCl3 DMSO-d6) δ 6.79 (s, 1H), 5.49 (d, 1H, J=15 Hz), 5.13 (d, 1H, J=15 Hz), 1.78 (q, 2H, J=6 Hz), 0.93 (t, 3H, J=9 Hz), IR (nujol) 3450, 1740, 1640, 1600, 1560, 1320, 1225, 1140, 1035, 995, 940 cm$^{-1}$.

EXAMPLE 6

7-Oxopyrido[5,4-c]-2-oxo-3-ethyl-3-hydroxy-3,6-dihydropyran

A mixture of the chloropyridone prepared in Example 5 above (400 mg, 1.64 mmol) and sodium acetate (400 mg, 4.86 mmol) in 25 mL of ethanol was hydrogenated over 10% Pd/C (100 mg) at 42 psi for 4 h. The mixture was filtered through celite and the solids were washed with CH$_3$OH. The filtrate was concentrated and the residue was purified by radial PLC (silica gel, 5% CH$_3$OH/CHCl$_3$) to give the pure product (256 mg, 75%) as a white solid: mp 230°-232° C. (dec.). Recrystallization from CHCl$_3$/CH$_3$OH afforded an analytical sample: mp 232° C. (dec.). $^1$H NMR (300 MHz, CHCl$_3$/DMSO-d6) δ 7.30 (d, 1H, J=6 Hz), 6.49 (d, 1H, J=6 Hz), 5.42 (d, 1H, J=18 Hz), 5.12 (d, 1H, J=18 Hz), 1.79 (m, 2H), 0.91 (t, 3H, J=6 Hz); IR (nujol) 3300, 1750, 1640, 1620, 1555, 1065, 1030, 995, 805, cm$^{-1}$.

EXAMPLE 7

2-Chloro-3-quinolinecarboxaldehyde

To a solution of 0.46 mL (3.30 mmol) of diisopropylamine in 8 mL of THF at 0° C. was added 1.53 mL (3.30 mmol) of n-BuLi dropwise. After 20 min the solution was cooled to −78° C. and 2-chloroquinoline (491 mg, 3.0 mmol) was added neat. The mixture was stirred at −78° C. for 30 min, then dimethylformamide (0.39 mL, 5.04 mmol) was added dropwise and the reaction mixture was stirred an additional 30 min at this temperature. After quenching at −78° C. with glacial acetic acid (1 mL), the mixture was warmed to room temperature and diluted with ether (30 mL). The organic phase was washed with saturated NaHCO$_3$ solution (10 mL) and brine (10 mL), and was dried over MgSO$_4$. Concentration afforded 2-chloro-3-quinolinecarboxaldehyde (530 mg, 92%) as a light yellow solid (mp 145°-149° C.), which was used directly in the next step without further purification. Recrystallization from ethyl acetate afforded the pure compound as light yellow needles: mp 149°-150° C. (mp 148°-149° C. reported in Meth-Cohn, O.; Narhe, B.; Tarnowski, B. J. Chem. Soc. Perkin Trans. I 1981, 1520.). $^1$H NMR (300 MHZ, CDCl3) δ 10.57 (s, 1H), 8.77 (s, 1H), 8.08 (d, 1H, J=9 HZ), 8.0 (d, 1H, J=9 HZ), 7.90 (t, 1H, J=9 HZ), 7.67 (t, 1H, J=9 HZ); IR (nujol) 1685, 1575, 1045, 760, 745 cm$^{-1}$.

EXAMPLE 8

Preparation of 2-Chloro-3-quinolinecarboxaldehyde from acetanilide

Following a literature procedure (see Meth-Cohn, O.; Narhe, B.; Tarnowski, B. J. Chem. Soc. Perkin Trans. I 1981, 1520), phosphorus oxychloride (24.0 mL, 260 mmol) was added dropwise to an ice-cold solution of dimethylformamide (7.20 mL, 93.0 mmol) and the deep-red solution was stirred at 0° C. for 30 min. Acetanilide (5.0 g, 37.0 mmol) was added neat and the mixture was stirred at 0° C. for 30 min, then heated at 75° C. for 16 h. The cooled mixture was poured into 250 mL of ice-water and stirred at 0°-5° C. for 30 min. The product was filtered, washed with water, and recrystallized from ethyl acetate to give 5.2 g (74%) of 2-Chloro-3-quinoline-carboxaldehyde as a light yellow solid: mp 147°-149° C.

EXAMPLE 9

2-Iodo-3-quinolinecarboxaldehyde

A mixture of the aldehyde prepared in accordance with Example 7 or 8 above (5.0 g, 26.2 mmol), sodium iodide (10.0 g, 66.7 mmol) and concentrated HCl (1 mL) in 100 mL of CH$_3$CN was heated at reflux for 4.5 h. After removal of most of the solvent in vacuo, aqueous Na$_2$CO$_3$ was added until the mixture was basic, and the product was filtered and washed with water. The crude product was recrystallized from 95% ethanol to give 6.51 g (88%) of 2-iodo-3-quinolinecarboxaldehyde as off-white fluffy needles: mp 156°-157° C. (mp 150°-152° C. reported in Meth-Cohn, O.; Narhe, B.; Tranowski, B.; Hayes, R.; Keyzad, A.; Rhavati, S.; Robinson, A. J. Chem. Soc. Perkin Trans. I 1981, 2509). $^1$H NMR (300 MHz, CDCl3) δ 10.29 (s, 1H), 8.57 (s, 1H), 8.12 (d, 1H, J=9 Hz), 7.98 (d, 1H, J=9 Hz) 7.88 (t, 1H J=9 Hz), 7.68 (t, 1H, J=9 Hz); IR (nujol) 1680, 1610, 1570, 1555, 1315, 1020, 1005, 750, 740 cm$^{-1}$.

EXAMPLE 10

3-Hydroxymethyl- 2- iodoquinoline

To a stirred solution of 2-iodo-3-quinolinecarboxaldehyde (595 mg, 2.10 mmol) in 40 mL of CH$_3$OH at 0° C. was added NaBH$_4$ (86 mg, 2.31 mmol), and the mixture was stirred at 0° C. for 30 min. After concentrating the mixture to approximately one-half of its original volume, water (30 mL) was added and the mixture was allowed to stand at 5° C. overnight. The solids were filtered and the crude product (570 mg, 95%) was recrystallized from methanol to give 3-hydroxymethyl-2-iodoquinoline (505 mg, 84%) as colorless needles: mp 189°-190° C. $^1$H NMR (300 MHz, CDCl3) δ 8.19 (s, 1H), 7.99 (d, 1H, J=9 Hz), 7.87 (d, 1H, J=9 Hz), 7.68 (m, 1H), 7.58 (t, 1H, J=9 Hz), 5.45 (t, 1H, J=6 Hz), 4.66 (d, 2H, J=6 Hz); IR (nujol) 3350, 1580, 1320, 1125, 1060, 995, 755, 720, cm$^{-1}$.

EXAMPLE 11

3-Chloromethyl-2-iodoquinoline

To a stirred mixture of 3-hydroxymethyl-2-iodoquinoline prepared in accordance with Example 10 above (350 mg, 1.23 mmol) and triphenylphosphine (483 mg, 1.84 mmol) in 10 mL of dry DMF at −23° C. was added N-chlorosuccinimide (246 mg, 1.84 mmol), and the mixture was stirred for 1 h at −23° C. After the addition of 40 mL of dilute aqueous NaHCO₃, the mixture was extracted with ethyl acetate (20 mL) and then ether (2×15 mL). The combined organic extracts were washed successively with 20-mL portions of dilute NaHCO₃, water and brine, and were dried over MgSO₄. Concentration and purification of the residue by radial PLC (silica gel, 10% ethyl acetate/hexanes) afforded 312 mg (84%) of 3-chloromethyl-2-iodoquinoline as a white crystalline solid: mp 138°–140° C. Recrystallization from hexanes afforded an analytical sample as colorless needles: mp 139°–140° C. ¹H NMR (300 MHz, CDCl3) δ 8.17 (s, 1H), 8.07 (d, 1H, J=9 Hz), 7.84 (d, 1H, J=9 Hz), 7.75 (t, 1H, J=9 Hz), 7.62 (t, 1H, J=9 Hz), 4.80 (s, 1H); IR (nujol) 1585, 1555, 1260, 1010, 780, 755, 710 cm$^{-1}$.

EXAMPLE 12

8-(2'-Iodo-3'-quinolylmethyl)-7-oxopyrido [5,4-c]-2-oxo-3-ethyl-3-hydroxy-3,6-dihydropyran To a solution containing 45 mg (0.40 mmol) of potassium tert-butoxide in 4 mL of dry isopropyl alcohol at 25° C. was added 55 mg (0.26 mmol) of 7-oxopyrido [5,4-c]-2-oxo-3-ethyl-3-hydroxy-3,6-dihydropyran prepared in accordance with Example 6 above and the mixture was stirred at 25° C. for 30 min. A solution of 3-chloromethyl-2-iodoquinoline prepared in accordance with Example 11 above (104 mg, 0.35 mmol) in 1 mL of CH₃OH was added dropwise to the white suspension, and the resulting solution was heated at 75° C. for 24 h. After quenching the reaction mixture with saturated NH₄Cl, the solvents were removed under reduced pressure, and the residue was taken up in CH₂Cl₂ (20 mL) and washed with brine (2×10 mL). Concentration and purification of the residue by radial PLC (2% CH₃OH/CHCl3) gave the product (99 mg, 80%) as a white solid: mp 171°–174° C. (dec.). Recrystallization from ethyl acetate/hexanes afforded an analytical sample: mp 174° C. (dec.). ¹H NMR (300 MHz, CDCl3) δ 8.05 (d, 1H, J=Hz), 7.70–7.80 (m, 3H), 7.55–7.61 (m, 2H), 6.61 (d, 1H, J=9 Hz), 5.63 (d, 1H, J=15 Hz), 5.43 (d, 1H, J=15 Hz), 5.27 (d, 1H, J=9 Hz), 5.22 (d, 1H, J=9 Hz); IR (nujol) 3350, 1750, 1650, 1590, 1565, 1160, 1140, 1000, 750 cm$^{-1}$.

EXAMPLE 13

(+)-Camptothecin

A mixture of 8-(2'-iodo-3'-quinolylmethyl)-7-oxopyrido[5,4-c]-2-oxo-3-ethyl-3-hydroxy-3,6-dihydropyran prepared in accordance with Example 12 above (76 mg, 0.16 mmol), K₂CO₃ (44 mg, 0.32 mmol), tetrabutylammonium bromide (52 mg, 0.16 mmol) and Pd(OAc)₂ (3.6 mg, 0.016 retool) in 15 mL of dry acetonitrile under argon was heated at 90° C. for 5 h. TLC analysis of the reaction mixture showed a single spot which was highly U.V. active. The mixture was cooled, concentrated, and the residue was taken up in 30 mL of CHCl3 containing 10% CH₃OH. This was washed with two 10-mL portions of saturated aqueous NH₄Cl. The organic layer was dried over Na₂SO₄ and concentrated. The dark residue was subjected to radial PLC (silica gel, 4% CH₃OH/CHCl3), to give 17 mg of an orange solid which was shown by NMR analysis to be a mixture of impure (+)-camptothecin and tetrabutylammonium bromide. The aqueous washings were filtered to give a yellow solid which was purified by radial PLC (silica gel, 4% CH₃OH/CHCl3) to afford (+)-camptothecin (26 mg, 47%) as a yellow solid: mp 275°–277° C. (mp 275°–277° C. reported in Volman, R.; Danishefsky, S.; Eggler, J.; Soloman, D. M. J. Am. Chem. Soc. 1971, 93, 4074.).

The foregoing examples are illustrative of the present invention, and are not to be construed as limiting thereof. The invention is defined by the following claims, with equivalents of the claims to be included therein.

That which is claimed is:

1. A compound selected from the group consisting of compounds of Formula IX:

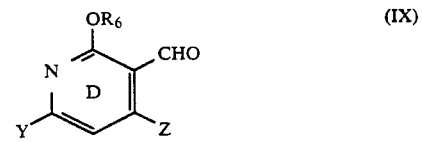

wherein:
R₆, is loweralkyl:
Y is Cl or H; and
Z is halogen.

2. A compound according to claim 1, wherein Z is bromo or iodo.

3. A compound according to claim 1, wherein R₆ is selected from the group consisting of methyl, ethyl, propyl, and butyl.

4. A compound according to claim 1, wherein R₆ is methyl.

5. A compound according to claim 1, wherein Z is iodo.

6. A compound according to claim 5, wherein R₆ is selected from the group consisting of methyl, ethyl, propyl, and butyl.

7. A compound according to claim 5, wherein R₆ is methyl.

8. A compound according to claim 1 or 5, wherein Y is CL.

9. A compound according to claim 1 or 5, wherein Y is H.

* * * * *

UNITED STATES PATENT AND TRADEMARK OFFICE
CERTIFICATE OF CORRECTION

PATENT NO. : 5,321,140

DATED : June 14, 1994

INVENTOR(S) : Daniel L. Comins; Matthew F. Baevsky

It is certified that error appears in the above-indentified patent and that said Letters Patent is hereby corrected as shown below:

Column 7, line 39, please correct " rain " to read -- min --.

Column 7, line 46, please correct " top " to read -- mp --.

Column 7, line 61, please correct " retool " to read -- mmol --.

Column 7, line 63, please correct " rain " to read -- min --.

Column 7, line 66, please correct " retool " to read -- mmol --.

Column 8, line 35, please correct " NA2 " to read -- $NA_2$ --.

Column 8, line 52, please correct " retool " to read -- mmol --.

Column 9, line 10, please correct " retool " to read -- mmol --.

Column 11, line 49, please correct " J=Hz " to read -- J=9Hz --.

UNITED STATES PATENT AND TRADEMARK OFFICE
CERTIFICATE OF CORRECTION

PATENT NO. : 5,321,140

DATED : June 14, 1994

INVENTOR(S) : Daniel L. Comins; Matthew F. Baevsky

It is certified that error appears in the above-indentified patent and that said Letters Patent is hereby corrected as shown below:

Column 12, line 2, please correct " retool " to read — mmol —.

Signed and Sealed this

Fourth Day of October, 1994

Attest:

BRUCE LEHMAN

Attesting Officer

Commissioner of Patents and Trademarks